United States Patent
Lee et al.

(10) Patent No.: US 10,292,614 B2
(45) Date of Patent: May 21, 2019

(54) WRIST-WEARABLE BODY COMPOSITION MEASURING DEVICE AND BODY COMPOSITION MEASURING METHOD USING THE SAME

(71) Applicant: SAMSUNG ELECTRONICS CO., LTD., Suwon-si (KR)

(72) Inventors: Yeolho Lee, Anyang-si (KR); Kak Namkoong, Seoul (KR); Kunsun Eom, Seoul (KR); Myounghoon Jung, Bucheon-si (KR); Seongho Cho, Gwacheon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 137 days.

(21) Appl. No.: 14/660,335

(22) Filed: Mar. 17, 2015

(65) Prior Publication Data
US 2016/0089053 A1  Mar. 31, 2016

(30) Foreign Application Priority Data
Sep. 26, 2014  (KR) .................. 10-2014-0129341

(51) Int. Cl.
*A61B 5/053*  (2006.01)
*A61B 5/00*  (2006.01)

(52) U.S. Cl.
CPC .......... *A61B 5/0537* (2013.01); *A61B 5/4872* (2013.01); *A61B 5/684* (2013.01); *A61B 5/6824* (2013.01)

(58) Field of Classification Search
CPC ..... A61B 5/681; A61B 5/0531; A61B 5/0537; A61B 5/6824
See application file for complete search history.

(56) References Cited

U.S. PATENT DOCUMENTS

| | | | |
|---|---|---|---|
| 6,950,695 B2* | 9/2005 | Chen ................. | A61B 5/02438 600/509 |
| 8,743,079 B2* | 6/2014 | Norieda ................. | G06F 1/163 345/156 |
| 9,526,433 B2* | 12/2016 | Lapetina .............. | A61B 5/6824 |

(Continued)

FOREIGN PATENT DOCUMENTS

| JP | 11-299752 | * 11/1999 |
|---|---|---|
| JP | 11-309123 A | 11/1999 |

(Continued)

*Primary Examiner* — Lee S Cohen
(74) *Attorney, Agent, or Firm* — Sughrue Mion, PLLC

(57) ABSTRACT

A wrist-wearable body composition measuring device includes a main body; a strap connected to the main body; a first input electrode and a first output electrode which are provided on an inner surface of the strap and configured to contact a wrist of a subject; a second input electrode and a second output electrode which are provided on an outer surface of the strap; a measuring unit configured to measure a body impedance of the subject by applying current to the first input electrode and the second input electrode and detecting a voltage generated between the first output electrode and the second output electrode in response to the applied current; and a processor configured to analyze a body composition of the subject based on the body impedance measured by the measuring unit.

12 Claims, 13 Drawing Sheets

(56) References Cited

U.S. PATENT DOCUMENTS

| | | | | |
|---|---|---|---|---|
| 2010/0076331 A1* | 3/2010 | Chan | A61B 5/0006 600/522 |
| 2014/0228666 A1* | 8/2014 | Ausin Sanchez | A61B 5/6831 600/384 |
| 2014/0323840 A1* | 10/2014 | Ouwerkerk | A61B 5/0531 600/390 |
| 2014/0335490 A1* | 11/2014 | Baarman | A61B 5/002 434/236 |
| 2015/0025353 A1* | 1/2015 | Salonius | A61B 5/0537 600/388 |
| 2015/0272483 A1* | 10/2015 | Etemad | A61B 5/05 600/409 |
| 2016/0058133 A1* | 3/2016 | Fournier | A61B 5/681 455/41.2 |
| 2016/0058375 A1* | 3/2016 | Rothkopf | A61B 5/681 600/301 |

FOREIGN PATENT DOCUMENTS

| | | | |
|---|---|---|---|
| JP | 2000-051173 A | | 2/2000 |
| KR | 1020010106959 | * | 12/2001 |

* cited by examiner

WRIST-WEARABLE BODY COMPOSITION MEASURING DEVICE AND BODY COMPOSITION MEASURING METHOD USING THE SAME

CROSS-REFERENCE TO RELATED APPLICATION

This application claims priority from Korean Patent Application No. 10-2014-0129341, filed on Sep. 26, 2014 in the Korean Intellectual Property Office, the disclosure of which is incorporated herein in its entirety by reference.

BACKGROUND

1. Field

Apparatuses and methods consistent with exemplary embodiments relate to a body composition measuring device and method.

2. Description of the Related Art

Along with the development of medical technologies and extension of the average lifespan, there has been an increasing interest in health care. In line with this, an interest in medical devices is also increasing. The range of such medical devices has expanded from various medical devices used in hospitals or health examination organizations to small-size and medium-size medical devices provided in public organizations and small-size medical devices and health care devices that are personally owned or carried.

A body composition measuring device, which is a sort of health care device, measures body composition using a bioelectrical impedance analysis (BIA) that obtains a ratio between quantities of fat and moisture by using the flow of low-energy alternating current (AC) waves based on an electric resistance difference between adipose tissues and non-adipose tissues. The BIA regards a human body as a combination of impedances, inputs current to the human body, and measures a voltage corresponding to a human body impedance to measure the human body impedance from the current and the voltage.

SUMMARY

Exemplary embodiments provide a wrist-wearable body composition measuring device and a body composition measuring method using the same.

According to an aspect of an exemplary embodiment, there is provided a wrist-wearable body composition measuring device, including a main body, a strap connected to the main body, a first input electrode and a first output electrode which are provided on an inner surface of the strap and configured to contact a wrist of a subject, a second input electrode and a second output electrode which are provided on an outer surface of the strap, a measuring unit configured to measure a body impedance of the subject by applying current to the first input electrode and the second input electrode and detecting a voltage generated between the first output electrode and the second output electrode in response to the applied current, and a processor configured to analyze a body composition of the subject based on the body impedance.

A direction in which a line intersecting the first input electrode and the first output electrode are arranged and a direction in which a line intersecting the second input electrode and the second output electrode are arranged may be perpendicular to a longitudinal direction of the strap.

A direction in which a line intersecting the first input electrode and the first output electrode are arranged and a direction in which a line intersecting the second input electrode and the second output electrode are arranged may be parallel to a longitudinal direction of the strap.

One direction among a direction in which a line intersecting the first input electrode and the first output electrode are arranged and a direction in which a line intersecting the second input electrode and the second output electrode are arranged may be parallel to a longitudinal direction of the strap, and the other of the directions is perpendicular to the longitudinal direction of the strap.

The measuring unit may include a current supply configured to supply the current to the first input electrode and the second input electrode, a voltage detector configured to detect the voltage generated between the first output electrode and the second output electrode, and an impedance calculator configured to calculate the body impedance of the subject based on the current and the voltage.

The wrist-wearable body composition measuring device may further include an inputter configured to receive information indicating at least one of a weight, an age, and a gender of the subject.

The inputter may be provided on the main body.

The wrist-wearable body composition measuring device may further include a storage configured to store an impedance of a body terminal part of the subject, where the second input electrode and the second output electrode are configured to contact the body terminal part when the body impedance is measured.

The processor may be configured to correct the body impedance based on the impedance of the body terminal part, and analyze the body composition of the subject based on the corrected body impedance.

The body composition may include at least one of body fat, body water, muscle strength, and an existence or absence of edema of the subject.

The wrist-wearable body composition measuring device may further include a display configured to display information about the body composition of the subject analyzed by the processor.

The display may be provided on the main body.

The wrist-wearable body composition measuring device may further include a transmitter configured to transmit information about the body composition of the subject to an external device.

According to an aspect of another exemplary embodiment, there is provided a body composition measuring method using a wrist-wearable body composition measuring device, the body composition measuring method including measuring and storing an impedance of at least one body terminal part of a subject, receiving information about the at least one body terminal part, measuring a body impedance while bringing the at least one body terminal part into contact with an input electrode of the wrist-wearable body composition measuring device and an output electrode of the wrist-wearable body composition measuring device, determining whether correction is required based on the received information, correcting the measured body impedance by using the stored impedance of the at least one body terminal part in response to determining that correction is required, and analyzing the body composition of the subject based on the body impedance.

The measuring and storing the impedance may include measuring the body impedance while bringing the at least one body terminal part, which is connected to a wrist of the subject, on which the wrist-wearable body composition measuring device is not worn, into contact with the input electrode and the output electrode, and storing a result of the measuring as a first impedance, measuring the body impedance while bringing the wrist of the subject into contact with the input electrode and the output electrode and storing a result of the measuring as a second impedance, and calculating an impedance of the body terminal part based on the first impedance and the second impedance.

The body composition measuring method may further include repeating the storing of the result of the measuring as the first impedance, the storing of the result of the measuring as the second impedance, and the calculating of the impedance, while changing the body terminal part which is connected to the wrist of the subject with another body terminal part.

The measuring operation may be performed when one of the body terminal parts contacts the input electrode and the output electrode at the same time, or when two body terminal parts contact the input electrode and the output electrode at the same time, respectively.

The body composition measuring method may further include converting information about the body composition of the subject analyzed in the analyzing operation into image information and displaying the image information.

The displaying the image information may include displaying the image information on a display provided on the wrist-wearable body composition measuring device or provided on an external device.

The body composition measuring method may further include transmitting information about the body composition of the subject analyzed in the analyzing to an external device.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1A:
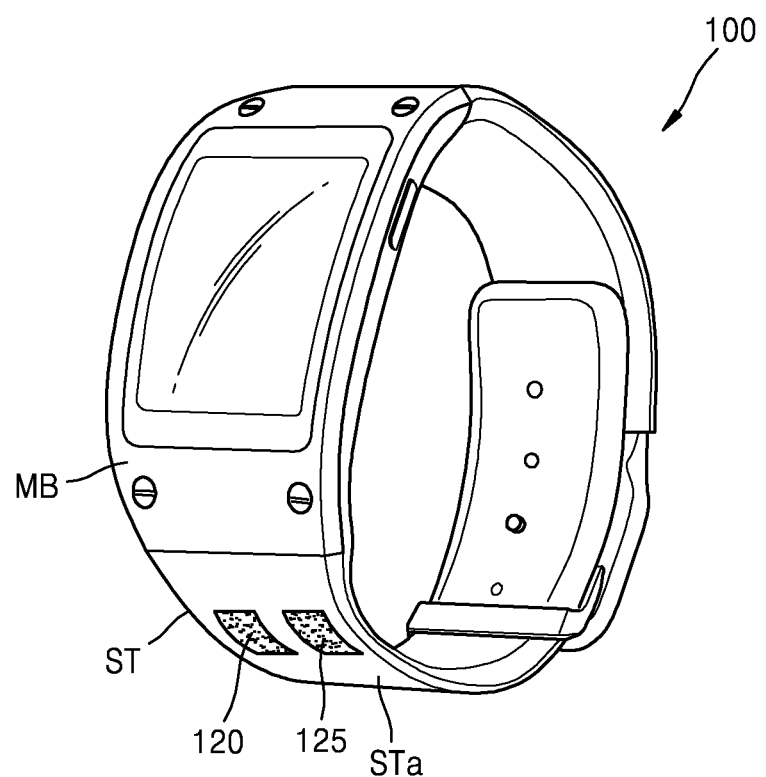
FIGS. 1A and 1B are perspective views of an appearance of a wrist-wearable body composition measuring device according to an exemplary embodiment, showing an outer surface and an inner surface of a strap, respectively.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. Expressions such as "at least one of," when preceding a list of elements, modify the entire list of elements and do not modify the individual elements of the list.

In the following description, when a layer, region, or component is referred to as being "above" or "on" another layer, region, or component, the layer, region, or component can be directly or indirectly on the other layer, region, or component.

In the following exemplary embodiments, terms such as "first", "second", and so forth are used only for distinguishing one component from another component, rather than for restrictive meanings.

In the following exemplary embodiments, the terms "comprises", "includes" and/or "has", when used in this specification, specify the presence of a stated feature, number, step, operation, component, element, or a combination thereof but do not preclude the presence or addition of one or more other features, numbers, steps, operations, components, elements, or combinations thereof.

Figure 1B:
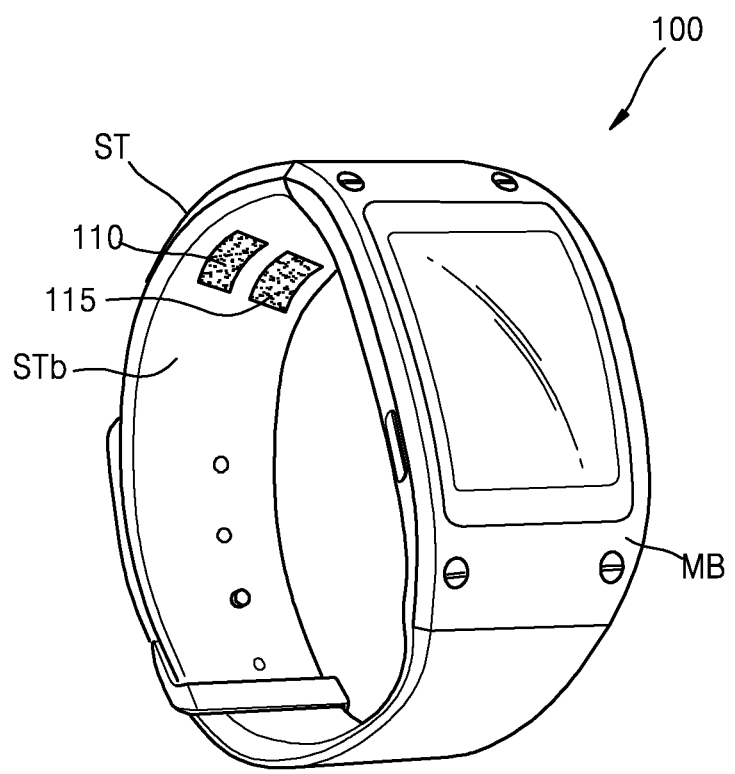
Figure 2:
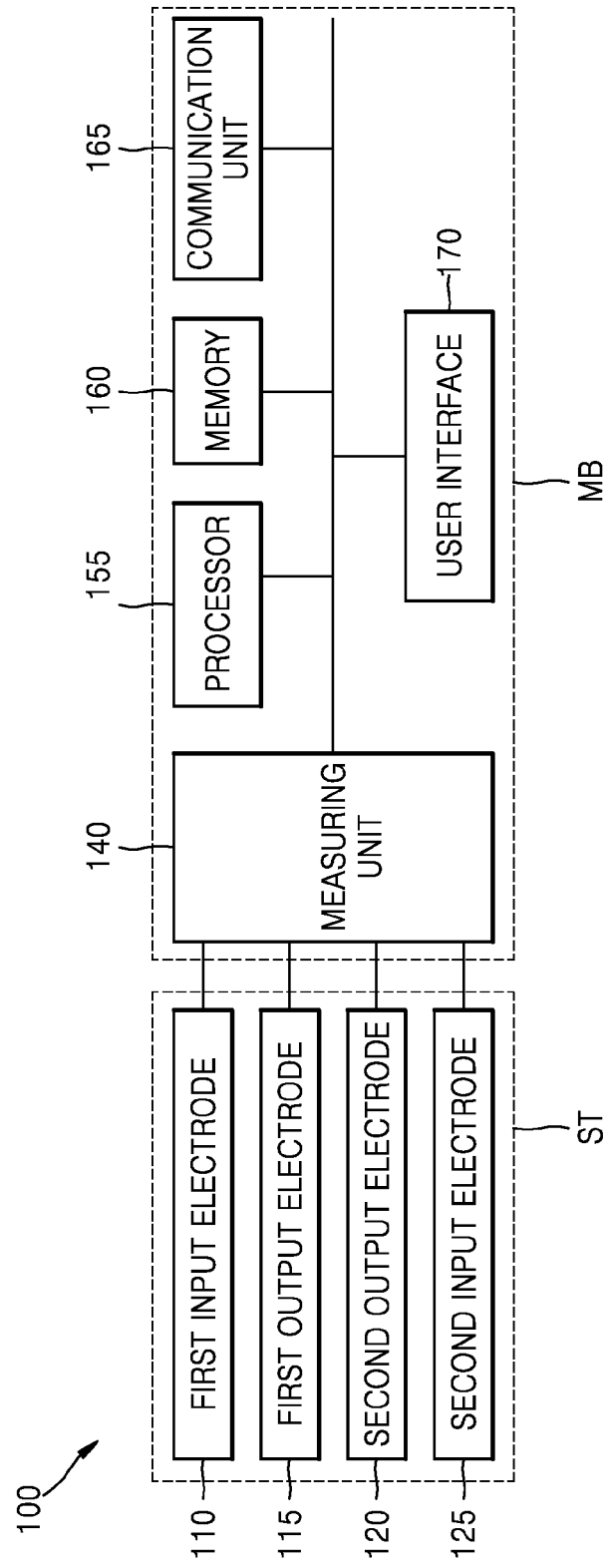
FIG. 2 is a block diagram of a wrist-wearable body composition measuring device according to an exemplary embodiment.
Figure 3:
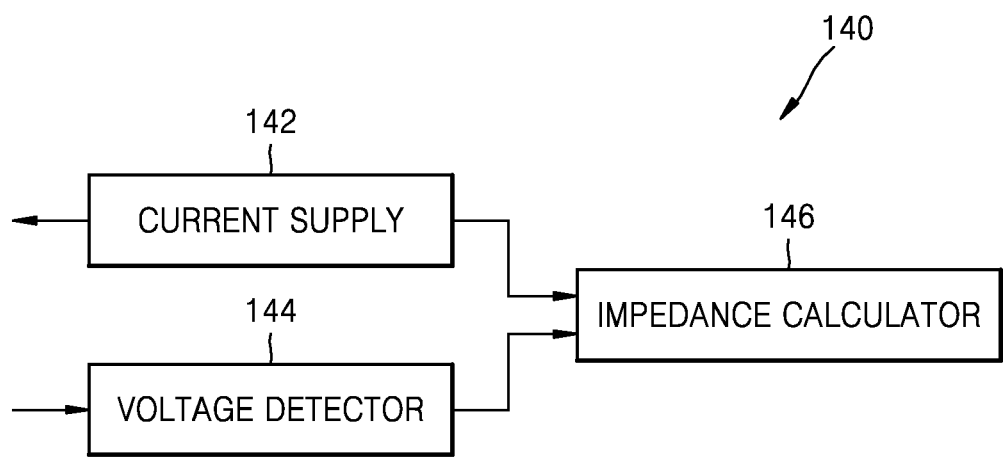
FIG. 3 is a block diagram of a measuring unit used in the wrist-wearable body composition measuring device of FIG. 2.

FIGS. 1A and 1B are perspective views of an appearance of a wrist-wearable body composition measuring device 100 according to an exemplary embodiment, showing an outer surface and an inner surface of a strap, respectively. FIG. 2 is a block diagram of the wrist-wearable body composition measuring device 100 according to an exemplary embodiment. FIG. 3 is a block diagram of a measuring unit 140 used in the wrist-wearable body composition measuring device 100 of FIG. 2.

Referring to FIGS. 1A through 3, the wrist-wearable body composition measuring device 100 may include a main body MB and the strap ST. The strap ST is provided as two strap parts at both sides of the main body MB, such that the strap ST is connected with the main body MB and is wearable on a wrist of a subject. A first input electrode 110 and a first output electrode 115 are formed on an inner surface STb of one of the two strap ST parts, and a second output electrode 120 and a second input electrode 125 are formed on an outer surface STa of the strap ST part.

A direction in which the first input electrode 110 and the first output electrode 115 are arranged on the inner surface STb of the strap ST part and a direction in which the second output electrode 120 and the second input electrode 125 are arranged on the outer surface STa of the strap ST part may be, but is not limited to, a direction perpendicular to a longitudinal direction of the strap ST part.

The first input electrode 110, the first output electrode 115, the second output electrode 120, and the second input electrode 125 all are provided on one of the two strap ST parts. In particular, the second output electrode 120 and the second input electrode 125, which require contact with a body part of a subject in measurement, are formed on the same strap ST part, thus improving user convenience.

The first input electrode 110 and the first output electrode 115 are shown as facing the second input electrode 125 and the second output electrode 120, respectively, but such illustration is exemplary only, and the first input electrode 110 and first output electrode 115 may not face each other according to other exemplary embodiments.

The first input electrode 110 and the first output electrode 115 contact a wrist of the subject when the wrist-wearable body composition measuring device 100 is worn by a user, that is, the subject whose body composition is to be measured. The first input electrode 110 is an electrode to which current is applied, and the first output electrode 115 is an electrode for measuring an output voltage.

The second output electrode 120 and the second input electrode 125 contact a body terminal part of the other wrist on which the wrist-wearable body composition measuring device 100 is not worn. The second input electrode 125 is an electrode to which current is applied, and the second output electrode 120 is an electrode for measuring an output voltage. A finger or a side of a hand may contact the second output electrode 120 and the second input electrode 125. To perform measurements, different fingers may contact the second output electrode 120 and the second input electrode 125, respectively, or one finger may contact the second output electrode 120 and the second input electrode 125 at the same time.

The measuring unit 140 applies current to the first input electrode 110 and the second input electrode 125 and measures a voltage between the first output electrode 115 and the second output electrode 120 to measure a body impedance.

As shown in FIG. 3, the measuring unit 140 may include a current supply 142 that supplies current to the first input electrode 110 and the second input electrode 125, a voltage detector 144 that detects a voltage between the first output electrode 115 and the second output electrode 120, and an impedance calculator 146 that calculates a body impedance of the subject by using the input current and the detected voltage. The voltage detector 144 may include an operation amplifying unit that amplifies a voltage between the first output electrode 115 and the second output electrode 120 and a filter that removes noise.

The body impedance measured by the measuring unit 140 may be used in a body composition analysis of the subject, performed by the processor 155. For example, the processor 155 may execute a program stored in a memory 160 to perform a body composition analysis.

The processor 155 may be hardware for controlling the overall function and operation of the wrist-wearable body composition measuring device 100. The processor 155 executes the program stored in the memory 160 to analyze a body composition using the body impedance measured by the measuring unit 140. Herein, the body composition may include body fat, skin characteristics (for example, body water), muscle strength, the existence or absence of edema of the subject, and the like. The operation of analyzing the body composition from the body impedance is well known and thus will not be described in detail.

The processor 155 analyzes the body composition from the body impedance, controls the measuring unit 140 to measure the body impedance, and processes the body composition analysis result into an image signal for display.

The processor 155 may be implemented in the form of one microprocessor module or a combination of two or more microprocessor modules. That is, the implementation form of the processor 155 is not limited thereto.

The memory 160 may store a program for the operation of the wrist-wearable body composition measuring device 100 and data necessary for the program. The memory 160 is a general storage medium, for example, a hard disk drive (HDD), read only memory (ROM), random access memory (RAM), a flash memory, a memory card, or the like.

The memory 160 may store a program for correcting the body impedance measured by the measuring unit 140, a program for analyzing the body composition based on the corrected body impedance, and the like. The memory 160 may also store additional data such as the height, weight, and gender of the subject, and the like. The memory 160 may also store an impedance for each body terminal part of the subject, such as a finger impedance, which may be used for correction of the body impedance.

A user interface 170 receives an input for manipulating the wrist-wearable body composition measuring device 100 from the subject and outputs information about the body composition of the subject processed by the processor 155. The user interface 170 may include an input unit (e.g., inputter) for allowing the user to manipulate the wrist-wearable body composition measuring device 100 and an output unit for outputting a result of the wrist-wearable body composition measuring device 100.

The user interface 170 may include a button, a keypad, a switch, a dial, a touch interface, or the like via which the subject directly manipulates the wrist-wearable body composition measuring device 100. The user interface 170 may include a display unit for displaying an image and may be implemented with a touch screen. The display unit may include a display panel such as a liquid crystal display (LCD) panel, an organic light-emitting diode (OLED) panel, or the like, and displays information about the analyzed body composition analysis result in the form of an image or a text. The user interface 170 may include an input/output (I/O) port for connecting human interface devices (HID) and may include an I/O port for inputting/outputting an image.

The user inputs the additional data, such as the height, weight, and gender of the subject, and obtains information about the measured body composition result, through the user interface 170.

The wrist-wearable body composition measuring device 100 may further include a communication unit 165 (e.g., a transceiver or a transmitter) for providing measured body impedance information or analyzed body composition information to an external device. The communication unit 165 may be connected with the external device in a wired or wireless manner. For example, the communication unit 165 may communicate with the external device using at least one of the communication protocols including, but not limited to, Bluetooth® communication, Bluetooth® low energy (BLE) communication, near field communication (NFC), wireless local area network (WLAN) communication, wireless fidelity (WiFi) communication, ZigBee communication, infrared data association (IrDA) communication, Wi-Fi direct (WFD) communication, ultra-wideband (UWB) communication, Ant+ communication, and the like. The external device may be a printer for printing a body composition analysis result, a display device for displaying the body composition analysis result, or another analysis device for analyzing a body composition based on a measured body impedance. The analysis device may be implemented in the form of a portable terminal carried by the user.

As shown in FIG. 2, the first input electrode 110, the second output electrode 120, the first output electrode 115, and the second input electrode 125 are disposed on the strap ST, and the measuring unit 140, the processor 155, the memory 160, the communication unit 165, and the user interface 170 may be disposed on the main body MB. However, the structure of the wrist-wearable body composition measuring device 100 is not limited to this example.

The main body MB may further include a watch module, so that the wrist-wearable body composition measuring device 100 may also be used as a watch.

Figure 4:
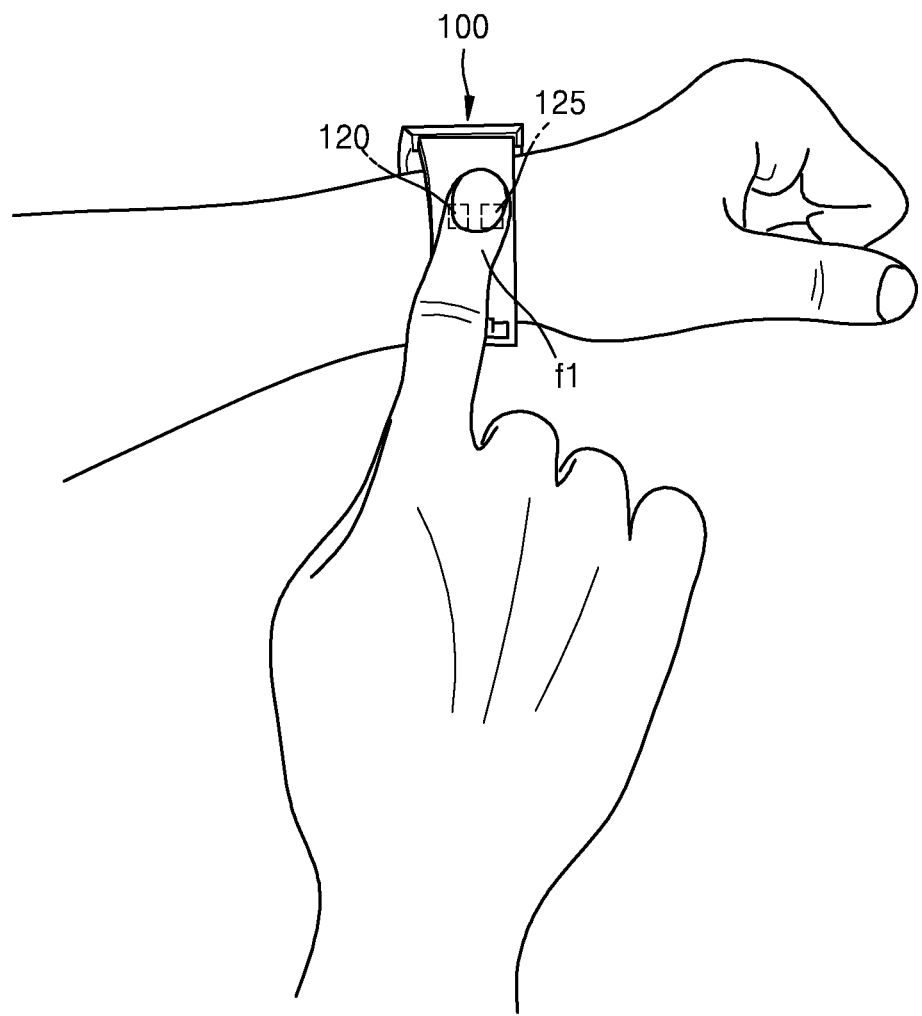
FIG. 4 shows an example of a body composition measuring posture used in connection with a wrist-wearable body composition measuring device according to an exemplary embodiment.
Figure 5:
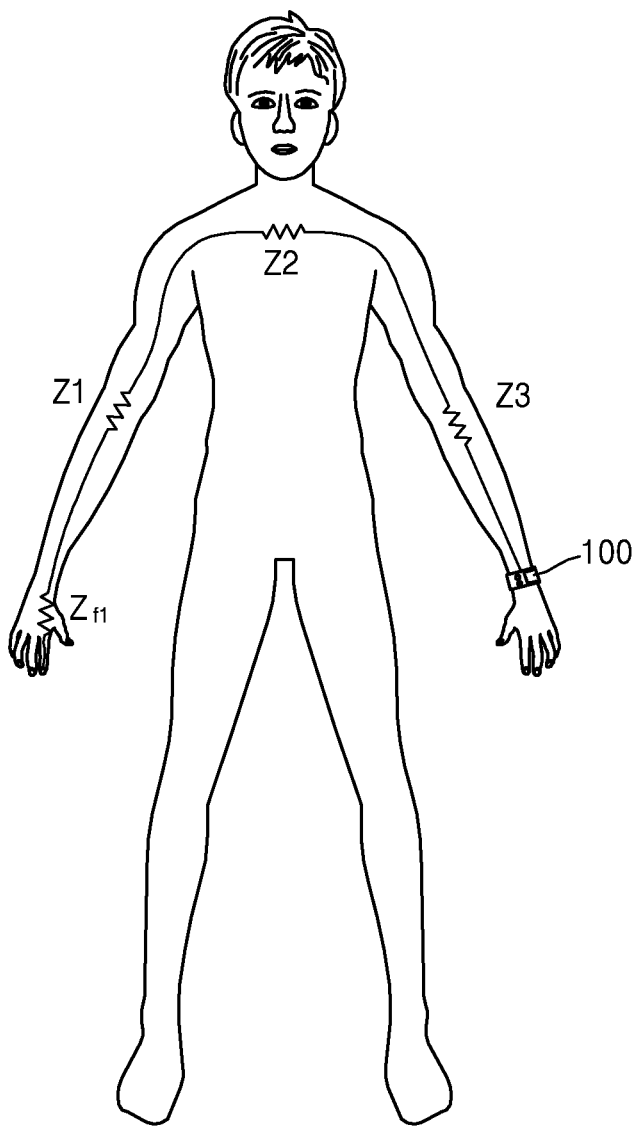
FIG. 5 schematically shows an equivalent impedance of a subject in the measurement posture of FIG. 4.
Figure 6:
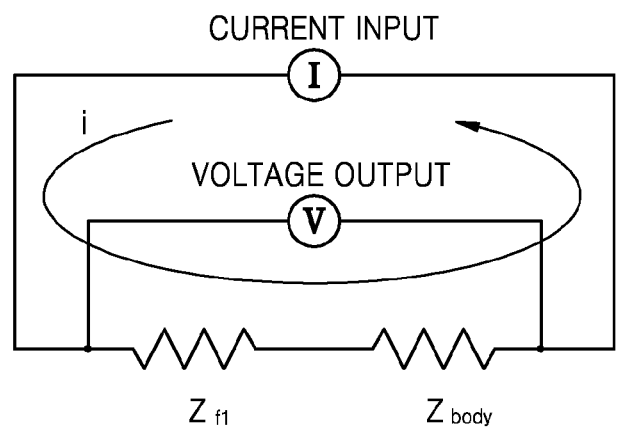
FIG. 6 is an equivalent circuit diagram for measuring a body impedance in the measurement posture of FIG. 4.

FIG. 4 shows an example of a body composition measuring posture using the wrist-wearable body composition measuring device 100 according to an exemplary embodiment. FIG. 5 schematically shows an equivalent impedance of the subject in the measurement posture of FIG. 4. FIG. 6 is an equivalent circuit diagram for measuring a body impedance in the measurement posture of FIG. 4.

Referring to FIG. 4, the subject wears the wrist-wearable body composition measuring device 100 on the left wrist of the subject and brings the right index finger f1 into contact with the second output electrode 120 and the second input electrode 125. It is understood that the postures are not limited to the example shown in FIG. 4, and for example, the wrist-wearable body composition measuring device 100 may instead be worn on the right wrist, or on another body part altogether, such as upper arm regions, calves, etc.

The equivalent impedance of the subject is as shown in FIG. 5. Impedances of the right arm, the body, and the left arm may be represented by Z1, Z2, and Z3, respectively, and a body impedance $Z_{body}$ equals to Z1+Z2+Z3. A resistance of the right index finger f1 used for measurements is $Z_{f1}$. Since the right index finger f1 contacts the second output electrode 120 and the second input electrode 125 at the same time, an impedance calculated from the voltage measured through the first output electrode 115 and the second input electrode 125 equals $Z_{body}+Z_{f1}$, as shown in FIG. 6. The impedance minus the impedance $Z_{f1}$ of the right index finger f1 equals the body impedance $Z_{body}$. The impedance $Z_{f1}$ of the right index finger f1 may be measured and stored in advance.

To perform measurements, the subject may use a finger such as the thumb, the middle finger, or the ring finger, other than the index finger, and in this case, the measured impedance may be corrected based on the thumb impedance or the middle finger impedance stored in advance to calculate the body impedance.

Figure 7:
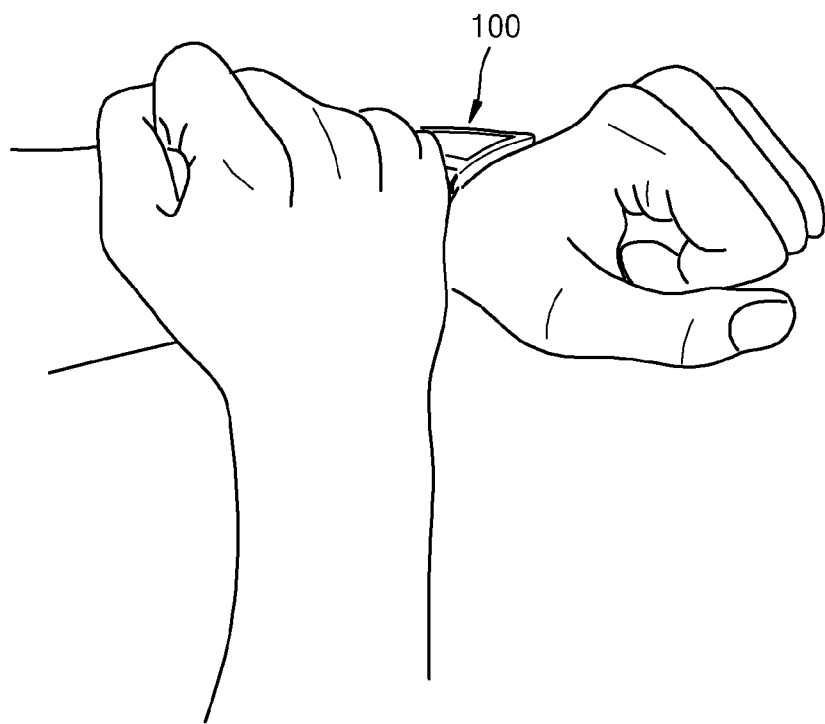
FIG. 7 shows another example of a body composition measuring posture used in connection with a wrist-wearable body composition measuring device according to an exemplary embodiment.

FIG. 7 shows another example of a body composition measuring posture using the wrist-wearable body composition measuring device 100 according to an exemplary embodiment.

The subject may bring a side of the fist of the right hand into contact with the second output electrode 120 and the second input electrode 125. If an impedance of the side of the fist of the right hand is stored in advance, it is possible to measure and correct impedance in this posture.

Figure 8:
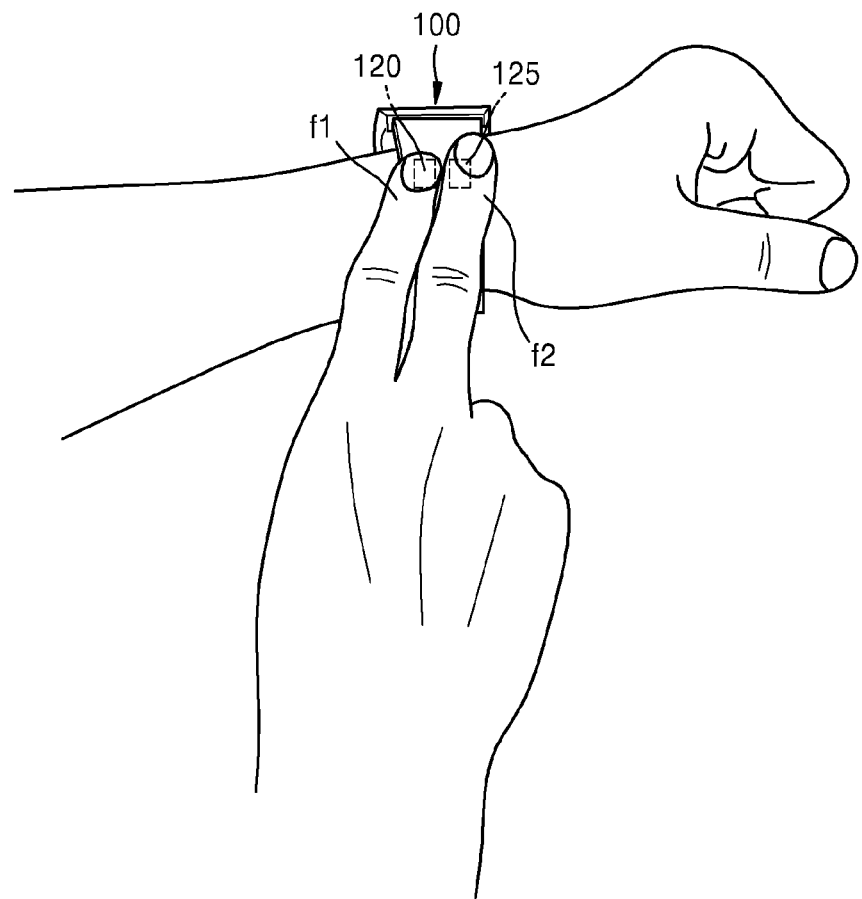
FIG. 8 shows another example of a body composition measuring posture used in connection with a wrist-wearable body composition measuring device according to an exemplary embodiment.
Figure 9:
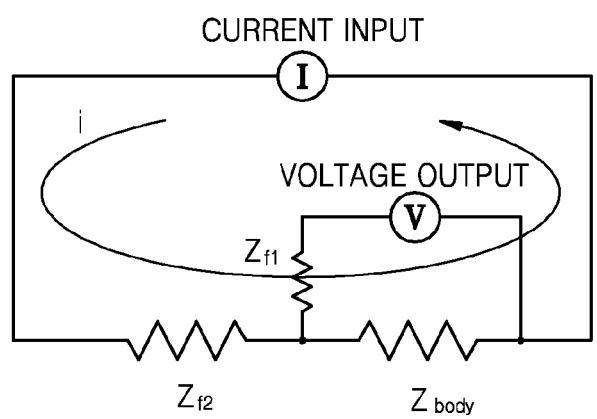
FIG. 9 is an equivalent circuit diagram for measuring a body impedance in the measurement posture of FIG. 8.

FIG. 8 shows another example of a body composition measuring posture using the wrist-wearable body composition measuring device 100 according to an exemplary embodiment, and FIG. 9 is an equivalent circuit diagram for measuring body impedance in the measurement posture of FIG. 8.

Referring to FIG. 8, the subject may bring the right index finger f1 and the right middle finger f2 into contact with the second output electrode 120 and the second input electrode 125, respectively.

Current applied between the first input electrode 110 and the second input electrode 125 flows along a closed circuit formed along the right middle finger f2, the right arm, the body, and the left arm, and no current flows along the right index finger f1. That is, no current flows in $Z_{f1}$. Thus, as shown in FIG. 9, an impedance measured based on the voltage measured between the first output electrode 115 and the second output electrode 120 is $Z_{body}$, and no correction is required.

Figure 10:
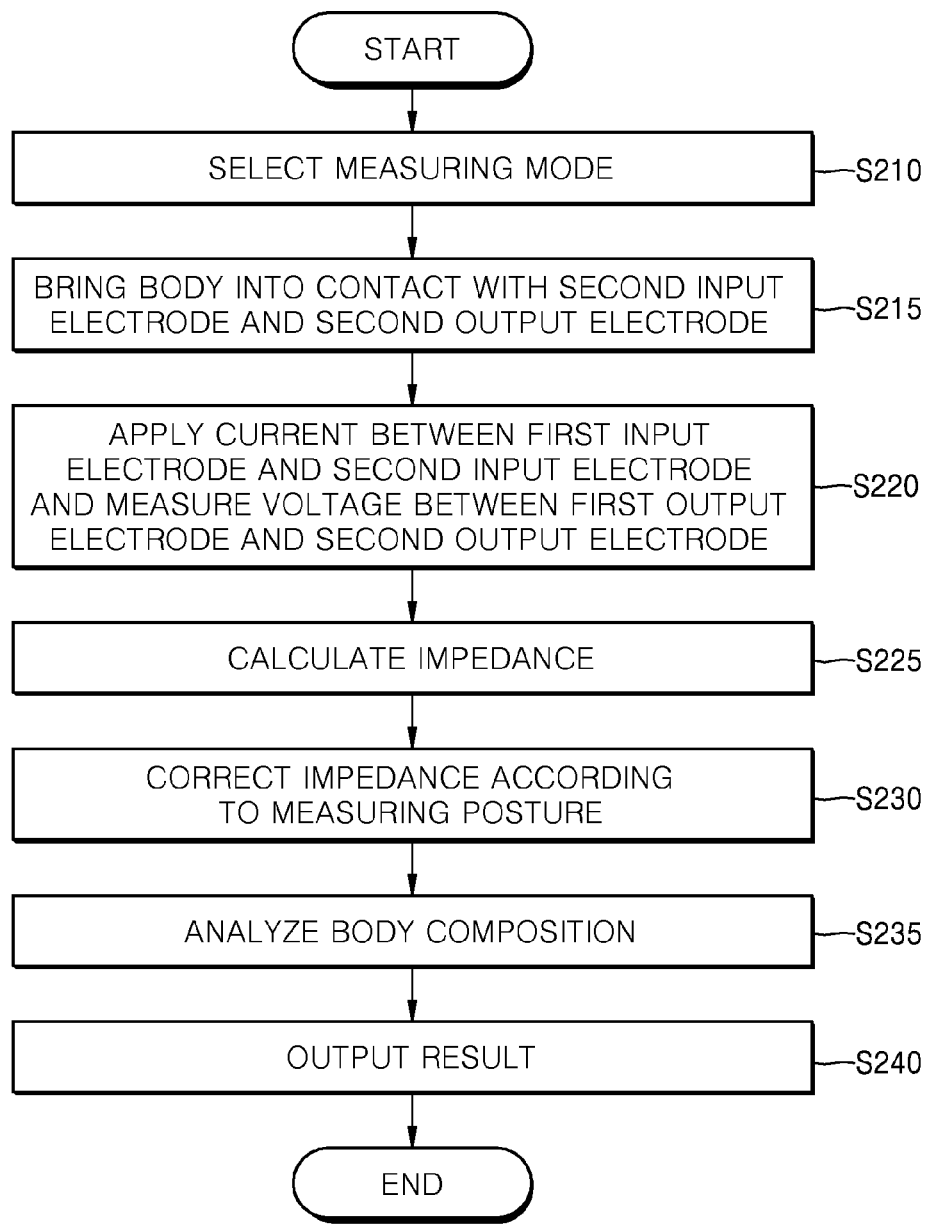
FIG. 10 is a flowchart of a body composition measuring method according to an exemplary embodiment.
Figure 11:
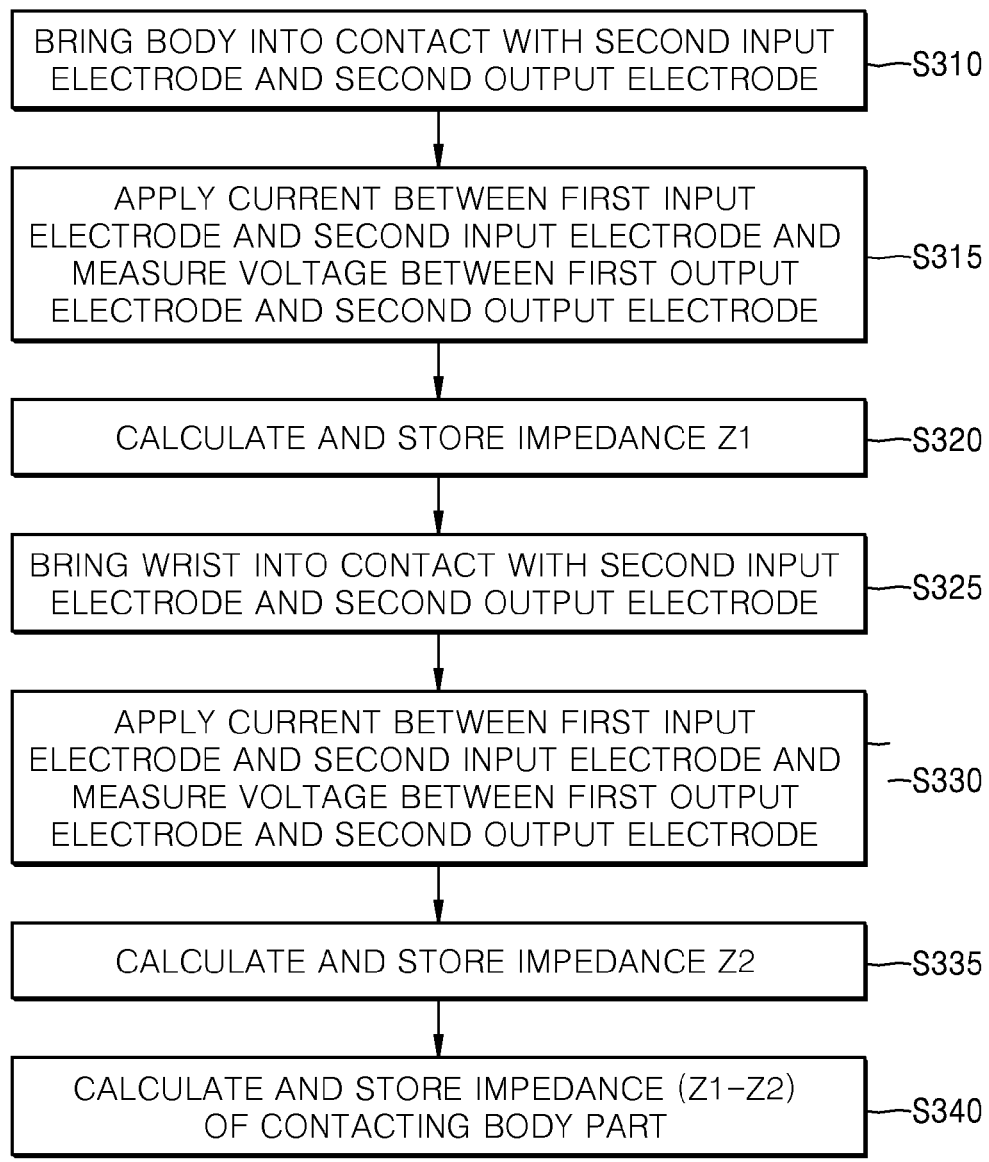
FIG. 11 is a flowchart of measuring an impedance at various body terminal parts for impedance correction in a body composition measuring method according to an exemplary embodiment.

FIG. 10 is a flowchart of a body composition measuring method according to an exemplary embodiment, and FIG. 11 is a flowchart of measuring impedance at various body terminal parts for impedance correction in a body composition measuring method, according to an exemplary embodiment.

To measure body composition, the subject wears the wrist-wearable body composition measuring device on, for example, the left wrist or the right wrist.

When a measuring mode is selected in operation S210, a measuring posture may be input and the height or weight of the subject may be input. As the measuring posture, contact by one finger or two fingers or information about a body terminal part that may contact the second input electrode or the second output electrode, for example, a finger type, for example, a thumb, an index finger, a ring finger, or the like, or a side of the fist, may be input.

In the measuring posture selected in the measuring mode, a body part contacts the second input electrode or the second output electrode in operation S220.

The measuring unit supplies current between the first input electrode and the second input electrode and measures a voltage between the first output electrode and the second output electrode in operation S225.

An impedance is calculated from the input current and the detected voltage in operation S230. The calculated impedance may be equal to $Z_a+Z_{body}$ or $Z_{body}$ according to the measuring posture, as described above. $Z_a$ indicates an impedance of a contacting body terminal part a.

Next, the impedance is corrected according to the measuring posture, that is, the contacting body terminal part, to calculate a body impedance in operation S230. In this operation, it is determined whether correction is required according to the contacting body terminal part, and if it is determined that correction is required, correction is performed. If one body terminal part, for example, a finger or a side of the palm contacts both the second input electrode and the second output electrode, correction using an impedance of the body terminal part is performed. If two fingers contact the second input electrode and the second output electrode, respectively, correction is not performed, as described with reference to the equivalent circuit of FIG. 9, and the calculated impedance is the body impedance.

In operation S235, a body composition is analyzed based on the obtained body impedance.

The analyzed body composition is output in the form of an image or a text in operation S240.

For impedance correction in operation S230, the impedance of the body terminal part a that is used in body composition measurement may be measured and stored in advance.

Referring to FIG. 11, the body terminal part a contacts the second input electrode and the second output electrode in operation S310. The body terminal part a may be, for example, fingers, the fist, or the palm of the left or right hand on which the wrist-wearable body composition measuring device is not worn.

In operation S315, current is supplied to the first input electrode and the second input electrode, and a voltage between the first output electrode and the second output electrode is measured.

The impedance Z1 is calculated from the input current and the output voltage and then stored.

The wrist of the hand, on which the wrist-wearable body composition wearing device is not worn, contacts the second input electrode and the second output electrode in operation S325.

Current is supplied to the first input electrode and the second input electrode and a voltage between the first output electrode and the second output electrode is measured in operation S330. The impedance Z2 is calculated from the input current and the output voltage and then stored.

The impedance of the body terminal part a is calculated from the stored impedances Z1 and Z2 and then stored in operation S340. The impedance of the body terminal part a equals Z1-Z2.

The foregoing operations may be repeated by changing hands, for example, the left hand with the right hand or vice versa, and changing body terminal parts, and the stored data may be used for body impedance correction.

Figure 12A:
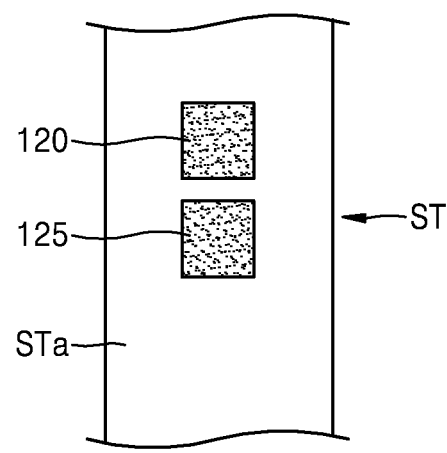
FIGS. 12A and 12B show another example in which a first input electrode, a first output electrode, a second input electrode, and a second output electrode are disposed on a strap of the body composition measuring device of FIG. 1.
Figure 12B:
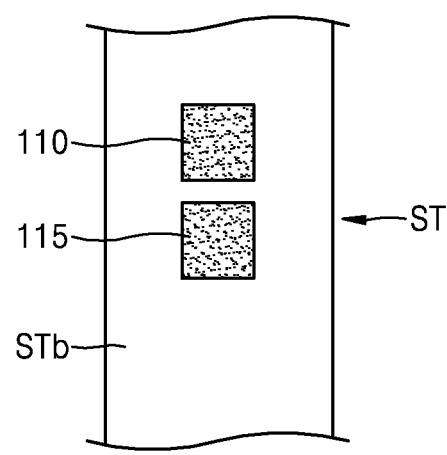

FIGS. 12A and 12B show another example in which the first input electrode 110, the first output electrode 115, the second input electrode 120, and the second output electrode 125 are disposed on the strap ST of the body composition measuring device 100 of FIG. 1.

Referring to FIGS. 12A and 12B, a direction in which the second output electrode 120 and the second input electrode 125 are arranged on the outer surface STa of the strap ST is the same as the longitudinal direction of the strap ST, and a direction in which the first input electrode 110 and the first output electrode 115 are arranged on the inner surface STb of the strap ST is also the same as the longitudinal direction of the strap ST.

The direction in which the first input electrode 110 and the first output electrode 115 are arranged may be different from the direction in which the second output electrode 120 and the second input electrode 125 are arranged.

Figure 13A:
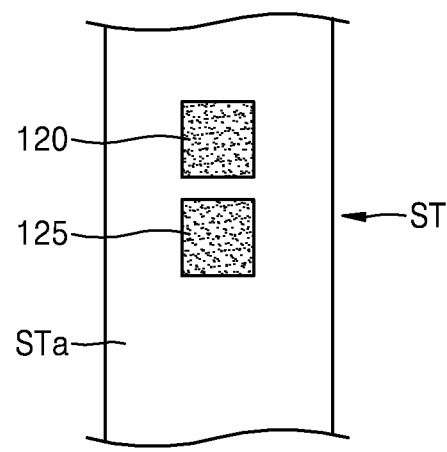
FIGS. 13A and 13B show still another example in which a first input electrode, a first output electrode, a second input electrode, and a second output electrode are disposed on a strap of the body composition measuring device of FIG. 1.
Figure 13B:
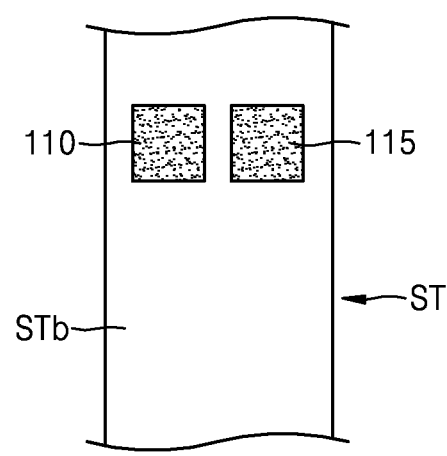

FIGS. 13A and 13B show still another example in which the first input electrode 110, the first output electrode 115, the second input electrode 120, and the second output electrode 125 are disposed on the strap ST of the body composition measuring device 100 of FIG. 1.

Referring to FIGS. 13A and 13B, a direction in which the second output electrode 120 and the second input electrode 125 are arranged on the outer surface STa of the strap ST is the same as the longitudinal direction of the strap ST, and a direction in which the first input electrode 110 and the first output electrode 115 are arranged on the inner surface STb of the strap ST is perpendicular to the longitudinal direction of the strap ST. The directions may be switched with each other on the inner surface STb and the outer surface STa of the strap ST.

Figure 14:
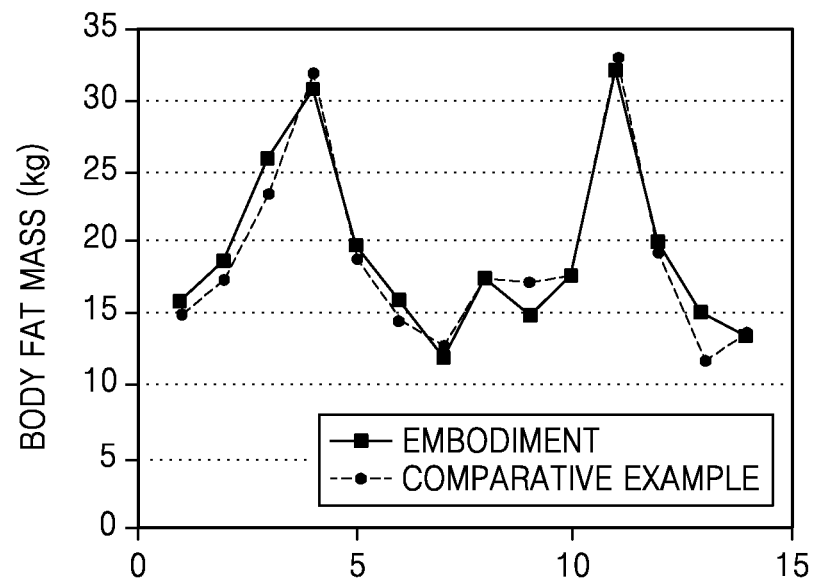
FIG. 14 is a graph showing body composition analysis results using body composition measuring devices according to an exemplary embodiment and a comparative example.
Figure 15:
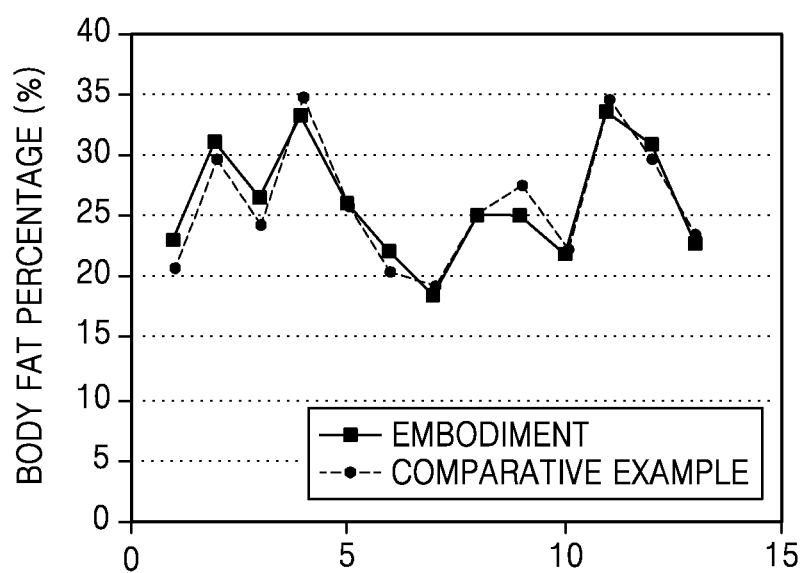
FIG. 15 is a graph showing body composition analysis results using body composition measuring devices according to an exemplary embodiment and a comparative example.

FIG. 14 is a graph showing body composition (body fat mass) analysis results using a body composition measuring device according to an exemplary embodiment and a comparative example, and FIG. 15 is a graph showing body composition (body fat percentage) analysis results using the body composition measuring device according to an exemplary embodiment and the comparative example.

The comparative example is a general-purpose measuring device. As can be seen from the graphs, analysis results of the wrist-wearable body composition measuring device according to an exemplary embodiment are similar with those of the comparative example.

As described above, according to the one or more of the above exemplary embodiments, the wrist-wearable body composition measuring device may be worn on a wrist of the subject and easily measure the body composition of the subject.

In the wrist-wearable body composition measuring device, four electrodes for measuring impedance or other values are all formed on the same strap part, thus improving user convenience.

Moreover, the impedances of various body parts according to a measuring posture of the subject may be stored in advance for use in correction of a measured value, thus increasing the degree of freedom of the measuring posture, and accordingly, improving user convenience.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While the wrist-wearable body composition measuring device and the body composition measuring method using the same according to one or more exemplary embodiments have been described with reference to the figures, it will be understood by those of ordinary skill in the art that various changes in form and details may be made therein without departing from the spirit and scope of the inventive concept as defined by the following claims.

What is claimed is:

1. A wrist-wearable body composition measuring device comprising:
   a main body;
   a strap connected to the main body;
   a first input electrode and a first output electrode which are provided on an inner surface of the strap and configured to contact a wrist of a first arm of a subject;
   a second input electrode and a second output electrode which are provided on an outer surface of the strap;
   a measuring unit configured to measure a body impedance of the subject by applying current to the first input electrode and the second input electrode and detecting a voltage generated between the first output electrode and the second output electrode in response to the applied current; and
   a processor configured to analyze a body composition of the subject based on the body impedance measured by the measuring unit,
   wherein the strap includes a first strap part and a second strap part that are spaced apart from each other, and the main body is disposed between the first strap part and the second strap part, the first input electrode and the first output electrode are disposed on the inner surface of the first strap part, and the second input electrode and the second output electrode are disposed on the outer surface of the first strap part, the first input electrode and the first output electrode on the inner surface of the first strap part are disposed to directly oppose the second input electrode and the second output electrode on the outer surface of the first strap part, to allow the measuring unit to measure the body impedance of the subject from a closed circuit that is formed when the wrist-wearable body composition measuring device is worn around the wrist of the first arm, the first input electrode and the first output electrode are pressed against the wrist of the first arm at a same time when the second input electrode and the second output electrode is contacted by at least one finger of a second arm of the subject, and there is no contact between the first arm and the second arm, and a direction in which the first input electrode and the first output electrode are arranged on the inner surface of the first strap part is perpendicular to a direction in which the second input electrode and the second output electrode are arranged on the outer surface of the first strap part.

2. The wrist-wearable body composition measuring device of claim 1, wherein the direction in which the first input electrode and the first output electrode are arranged on the inner surface of the first strap part is perpendicular to a longitudinal direction of the strap.

3. The wrist-wearable body composition measuring device of claim 1, wherein the direction in which the first input electrode and the first output electrode are arranged on the inner surface of the first strap part is parallel to a longitudinal direction of the strap.

4. The wrist-wearable body composition measuring device of claim 1, wherein the measuring unit comprises:
a current supply configured to supply the current to the first input electrode and the second input electrode;
a voltage detector configured to detect the voltage generated between the first output electrode and the second output electrode; and
an impedance calculator configured to calculate the body impedance of the subject based on the current and the voltage.

5. The wrist-wearable body composition measuring device of claim 1, further comprising an inputter provided on the main body and configured to receive information indicating at least one of a weight, an age, and a gender of the subject.

6. The wrist-wearable body composition measuring device of claim 5, wherein the inputter comprises a button.

7. The wrist-wearable body composition measuring device of claim 1, further comprising a storage configured to store an impedance of a body terminal part of the subject, wherein the second input electrode and the second output electrode are configured to contact the body terminal part when the body impedance is measured.

8. The wrist-wearable body composition measuring device of claim 7, wherein the processor is configured to correct the body impedance based on the impedance of the body terminal part, and analyze the body composition of the subject based on the corrected body impedance.

9. The wrist-wearable body composition measuring device of claim 1, wherein the body composition comprises body fat and body water of the subject.

10. The wrist-wearable body composition measuring device of claim 1, wherein the body composition comprises muscles of the subject and the processor is further configured to analyze a strength of the muscles of the subject.

11. The wrist-wearable body composition measuring device of claim 1, wherein the processor is further configured to analyze the body composition to determine whether the subject has edema.

12. The wrist-wearable body composition measuring device of claim 1, further comprising a transmitter configured to transmit information about the body composition of the subject to an external device.

* * * * *